United States Patent
Drescher et al.

(10) Patent No.: US 9,976,851 B2
(45) Date of Patent: May 22, 2018

(54) ACCURATE MACHINE TOOL INSPECTION OF TURBINE AIRFOIL

(71) Applicant: United Technologies Corporation, Hartford, CT (US)

(72) Inventors: Joseph D. Drescher, Middletown, CT (US); Erik M. Pedersen, Cheshire, CT (US)

(73) Assignee: United Technologies Corporation, Farmington, CT (US)

( * ) Notice: Subject to any disclaimer, the term of this patent is extended or adjusted under 35 U.S.C. 154(b) by 664 days.

(21) Appl. No.: 13/835,622

(22) Filed: Mar. 15, 2013

(65) Prior Publication Data

US 2013/0215260 A1    Aug. 22, 2013

Related U.S. Application Data (63) Continuation-in-part of application No. 12/772,510, filed on May 3, 2010, now Pat. No. 8,797,398.

(51) Int. Cl.

| | |
|---|---|
| *G01B 21/00* | (2006.01) |
| *G01B 11/00* | (2006.01) |
| *G01N 21/88* | (2006.01) |
| *G01N 21/956* | (2006.01) |

(52) U.S. Cl.
CPC .............. *G01B 21/00* (2013.01); *G01B 11/00* (2013.01); *G01N 21/8806* (2013.01); *G01N 21/95692* (2013.01)

(58) Field of Classification Search
CPC ............................. G01B 21/00; G01N 21/8806
USPC .................................. 348/92; 382/152, 141
See application file for complete search history.

(56) References Cited

U.S. PATENT DOCUMENTS

| | | | |
|---|---|---|---|
| 4,583,159 A | 4/1986 | Kanemoto et al. | |
| 4,807,296 A | 2/1989 | Ando et al. | |
| 4,955,269 A * | 9/1990 | Kendig ................. | G07C 3/00 73/114.07 |
| 5,111,590 A | 5/1992 | Park | |
| 5,114,230 A * | 5/1992 | Pryor ................. | G01B 11/2433 209/586 |
| 5,125,035 A * | 6/1992 | McCarthy ........ | G01N 21/95692 348/94 |

(Continued)

OTHER PUBLICATIONS

Google search for NPL log.*

(Continued)

*Primary Examiner* — Luis Perez Fuentes
(74) *Attorney, Agent, or Firm* — Carlson, Gaskey & Olds P.C.

(57) ABSTRACT

Inspecting features of an object including measuring features of the master part that represents a desired nominal dimensions to obtain a preliminary set of dimensional data. The preliminary set of data becomes a master data set. The same master part is measured on a second machine to obtain another set of data on the master part. The two data sets are compared and correction data is generated representing differences between the different data sets for the same master part measured on different machines. Subsequent parts are then measured on the second machine to obtain measurement data that is corrected based on the correction data. The application of the correction information provides for the use of 5-axis machines within a desired measurement capability.

13 Claims, 3 Drawing Sheets

(56) References Cited

U.S. PATENT DOCUMENTS

| | | | | |
|---|---|---|---|---|
| 5,670,879 | A * | 9/1997 | Zombo | G01N 27/9013 |
| | | | | 324/227 |
| 6,909,517 | B2 | 6/2005 | Coleman et al. | |
| 6,945,124 | B1 | 9/2005 | Leboeuf et al. | |
| 6,992,315 | B2 * | 1/2006 | Twerdochlib | F01D 5/005 |
| | | | | 250/330 |
| 7,116,839 | B2 | 10/2006 | Leboeuf et al. | |
| 7,138,629 | B2 * | 11/2006 | Noji | G01N 23/225 |
| | | | | 250/310 |
| 7,272,460 | B2 * | 9/2007 | Akiyama | G06F 17/5068 |
| | | | | 700/90 |
| 7,489,811 | B2 * | 2/2009 | Brummel | G01N 21/8806 |
| | | | | 382/152 |
| 7,574,035 | B2 * | 8/2009 | Koonankeil | F01D 5/005 |
| | | | | 348/86 |
| 7,610,170 | B2 | 10/2009 | Ko et al. | |
| 7,710,626 | B2 * | 5/2010 | Ito | G02B 7/003 |
| | | | | 359/200.8 |
| 7,970,488 | B2 | 6/2011 | Prestidge et al. | |
| 8,543,573 | B2 * | 9/2013 | MacPherson | G06N 5/02 |
| | | | | 707/736 |
| 2004/0004475 | A1 * | 1/2004 | Goldfine | G01N 27/902 |
| | | | | 324/242 |
| 2005/0151963 | A1 * | 7/2005 | Pulla | G01B 21/04 |
| | | | | 356/139.03 |
| 2006/0078193 | A1 * | 4/2006 | Brummel | G01N 21/8806 |
| | | | | 382/152 |
| 2007/0276629 | A1 | 11/2007 | Koonankeil | |
| 2009/0002695 | A1 * | 1/2009 | Saito | G01N 21/8806 |
| | | | | 356/237.4 |
| 2010/0188500 | A1 * | 7/2010 | Bouchard | G01N 21/8901 |
| | | | | 348/93 |
| 2012/0188380 | A1 | 7/2012 | Drescher et al. | |

OTHER PUBLICATIONS

Conjuction. (2007). In The American Heritage® Dictionary of the English Language. Retrieved from http://www.credoreference.com/entry/hmdictenglang/conjunction.

* cited by examiner

ACCURATE MACHINE TOOL INSPECTION OF TURBINE AIRFOIL

CROSS REFERENCE TO RELATED APPLICATION

This application is a continuation in part of U.S. application Ser. No. 12/772,510 filed on May 3, 2010.

BACKGROUND

A gas turbine engine typically includes a fan section, a compressor section, a combustor section and a turbine section. Air entering the compressor section is compressed and delivered into the combustion section where it is mixed with fuel and ignited to generate a high-speed exhaust gas flow. The high-speed exhaust gas flow expands through the turbine section to drive the compressor and the fan section. The compressor section typically includes low and high pressure compressors, and the turbine section includes low and high pressure turbines.

Turbine vanes and blades along with other components in the core flow path are exposed to the extreme temperatures of the exhaust gas flow. In order to protect the turbine blades and other elements in the exhaust gas flow path it is known to pass cooling air of the exposed surfaces. Cooling is facilitated with cooling passages that direct air to cooling openings arranged to direct cooling airflow of surfaces of the turbine airfoils and elements. The cooling openings are arranged in a specific manner and location to generate the desired layer of cool air. The cooling openings can be of different shapes, sizes and angular orientations. Accordingly, manufacture of these turbine airfoils and elements includes an inspection process that verifies that the openings are properly formed and located.

Conventional inspection procedures include a fixture for holding the turbine vane or element in a known orientation and utilize a video camera or probe movable relative to the turbine vane or element to obtain measurements of specific features. Each measurement is taken from a specific repeatable orientation. Therefore a coordinate measuring machine (CMM) that is specifically designed for the purpose of measuring parts is utilized. However, such machines are costly and typically specialized for specific parts and features.

Accordingly, it is desirable to develop and design alternate methods and systems of conducting the required measurements and inspections at reduced costs while maintaining the desired measurement capability.

SUMMARY

A method of inspecting features of an object according to an exemplary embodiment of this disclosure, among other possible things includes measuring features of a master part to obtain a preliminary set of dimensional data with a first measurement machine, comparing, by a controller, the preliminary set of dimensional data from a second measuring machine with a master set of dimensional data for the master part, defining, by the controller, correction information based on differences between the master set of dimensional data and the preliminary set of dimensional data, measuring features of an object part to obtain a first set of dimensional data, and applying the correction information to the first set of dimensional data to obtain a first set of corrected dimensional data for at least one feature of the object part.

In a further embodiment of the foregoing method, includes verifying the correction information by measuring the master part to obtain a verification set of dimensional data, applying the correction information to the verification set of data to generate a corrected verification data set and comparing the corrected verification data set to the expected data set for the master part.

In a further embodiment of any of the foregoing methods, the correction information is verified as meeting a desired capability responsive to a comparison between the expected data set and the corrected verification data being within a predefined range.

In a further embodiment of any of the foregoing methods, measuring the features of the master part and the object part includes the step of moving a camera with a manipulator to view each feature measured.

In a further embodiment of any of the foregoing methods, measuring the features of the master part and the object part includes the step of moving a touch sensitive probe to each feature measured.

In a further embodiment of any of the foregoing methods, the preliminary set of dimensional data includes a plurality of measurements performed on each feature of the master part.

In a further embodiment of any of the foregoing methods, the master set of dimensional data is obtained by measuring the master part on the first measurement machine with a known measurement capability, and a preliminary set of dimensional data is measured on the second machine of an unknown measurement capability.

In a further embodiment of any of the foregoing methods, includes obtaining data indicative of measurement repeatability of the second machine and utilizing the data indicative of measurement repeatability to define the correction information.

In a further embodiment of any of the foregoing methods, the correction information defines differences between measurement results obtained on the first measurement machine and measurement results obtained from the second machine.

In a further embodiment of any of the foregoing methods, the second machine facilitates movement of an inspection device along five (5) axes.

In a further embodiment of any of the foregoing methods, the object part includes an airfoil and the features include cooling holes and the inspection results include at least one of a cooling hole size and true position of the cooling holes relative to a part coordinate system.

A inspection system for measuring a plurality of features of a target article according to an exemplary embodiment of this disclosure, among other possible things includes a measurement device for measuring features of an article, and a controller for storing measurement data obtained by the measurement device. The controller includes correction information and a combination module for applying the correction information to the measurement data to generate a corrected set of measurement data.

In a further embodiment of the foregoing inspection system, the controller further includes a comparison module for comparing a master set of measurement data obtained with a coordinate measurement machine and a preliminary set of measurement data obtained by the measurement device and generating the correction information based on results of the comparison.

In a further embodiment of any of the foregoing inspection systems, the measurement device is part of a machine tool different than the coordinate measurement machine and the correction information includes information indicative in a difference between measurement capabilities of the coordinate measurement machine and the machine tool.

In a further embodiment of any of the foregoing inspection systems, the comparison module applies a correction factor to measured data by the measurement device of the machine tool for generating the corrected set of measurement data within a desired range of capability.

In a further embodiment of any of the foregoing inspection systems, includes a master part for obtaining the master data set on the coordinate measurement machine and the preliminary data set from the machine tool.

In a further embodiment of any of the foregoing inspection systems, the machine tool includes a 5-axis machine tool.

Although the different examples have the specific components shown in the illustrations, embodiments of this disclosure are not limited to those particular combinations. It is possible to use some of the components or features from one of the examples in combination with features or components from another one of the examples.

These and other features disclosed herein can be best understood from the following specification and drawings, the following of which is a brief description.

DETAILED DESCRIPTION

Figure 1:
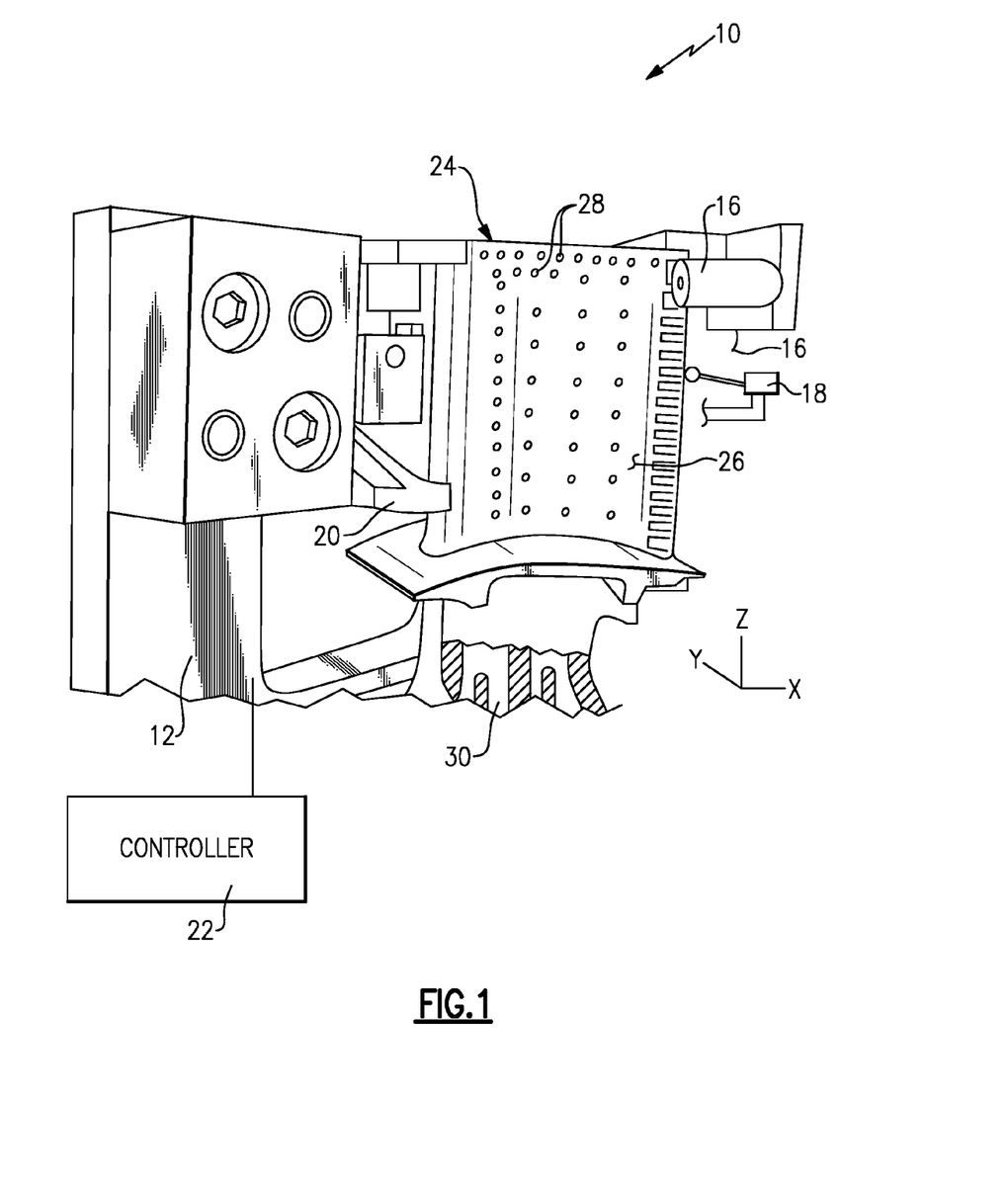
FIG. 1 is a schematic view of an inspection machine, in an embodiment.

FIG. 1 schematically illustrates an example machine tool inspection system generally indicated at 10. The example system 10 utilizes a 5-axis machine tool 12 to perform inspection of an object 24 such as a turbine blade at a production speed or "on-the-fly". As appreciated, the turbine blade includes a plurality of openings 28 that extend through a surface 26. The turbine blade also includes various air passages 30 that supply air to the cooling openings 28. The location of each of the cooling openings 28 must be verified by an inspection of each turbine blade during production. The position of each of the cooling holes 28 is important to provide the specific cooling features designed for each specific turbine blade. Accordingly, an accurate and capable measuring machine that provides measurements "on-the-fly" of a production part within a desired measurement capability is required.

Measurement capability is term utilized to refer to a measure of the ability of a machine or process to produce an output within a desired range. In this disclosure, the term capability refers to a measurement machine, CMM or machine tool, ability to repeat measurements within a desired range of accuracy.

Coordinate measuring machines (CMM) are typically required for such accurate measurements of features on the production part 24. However, a coordinate measuring machine of the capability required to provide the measurements of each of the openings 28, can be costly. Moreover, measurements performed on a CMM machine are typically to slow for production applications. Instead, CMM machines are typically utilized for limited inspection applications. A machine tool, such as a 5-axis capable machine tool, utilized for machining and forming parts has a high level of repeatability and speed, but may not be as capable of positioning a measurement device when compared to a specialized CMM. The disclosed method and system utilizes a five axis machine 12 in concert with correction information to generate measurement data within a desired capability.

The 5-axis machine 12 is typically not accurate to the capability required for inspection of each of the openings 28. However, the same 5-axis machine has sufficient repeatability of positioning a tool or in this instance a camera 16 and/or probe 18, to provide the desired inspection of the openings 28. Moreover, the 5-axis machine can measure parts at faster rates that better correspond with a production environment. A controller 22 operated in concert with the 5-axis machine 12 is programmed to obtain measurements and apply a correction to those measurements based on previously gathered and stored information.

The example controller 22 includes correction information 42 (FIG. 2) that provides correction information to correlate inspection information obtained from the 5-axis machine 12 with a more accurate CMM.

Figure 2:
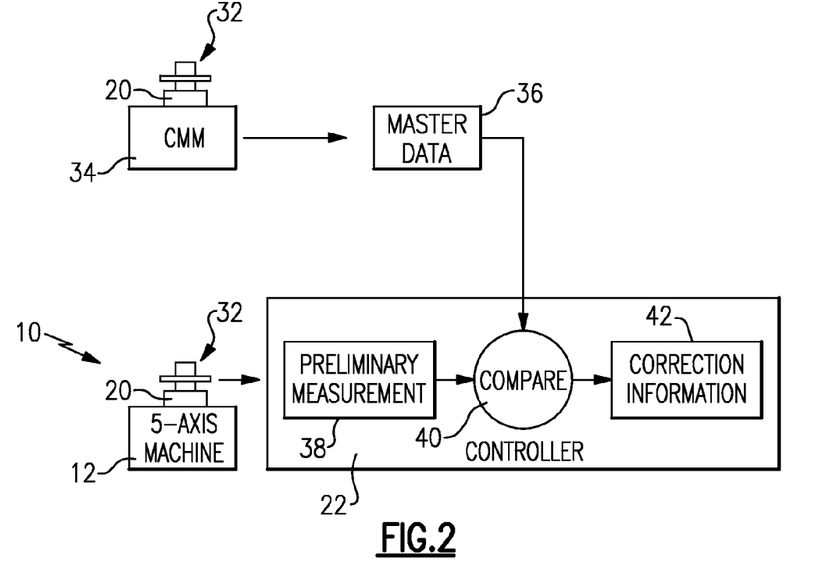
FIG. 2 is a schematic view of a process for obtaining correction information, in an embodiment.
Figure 3:
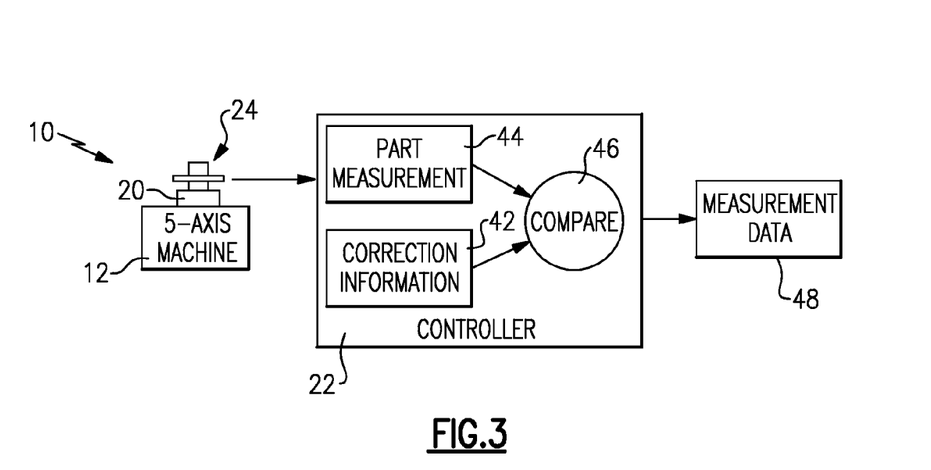
FIG. 3 is a schematic representation of a method of measuring with a machine tool utilizing correction information, in an embodiment.
Figure 4:
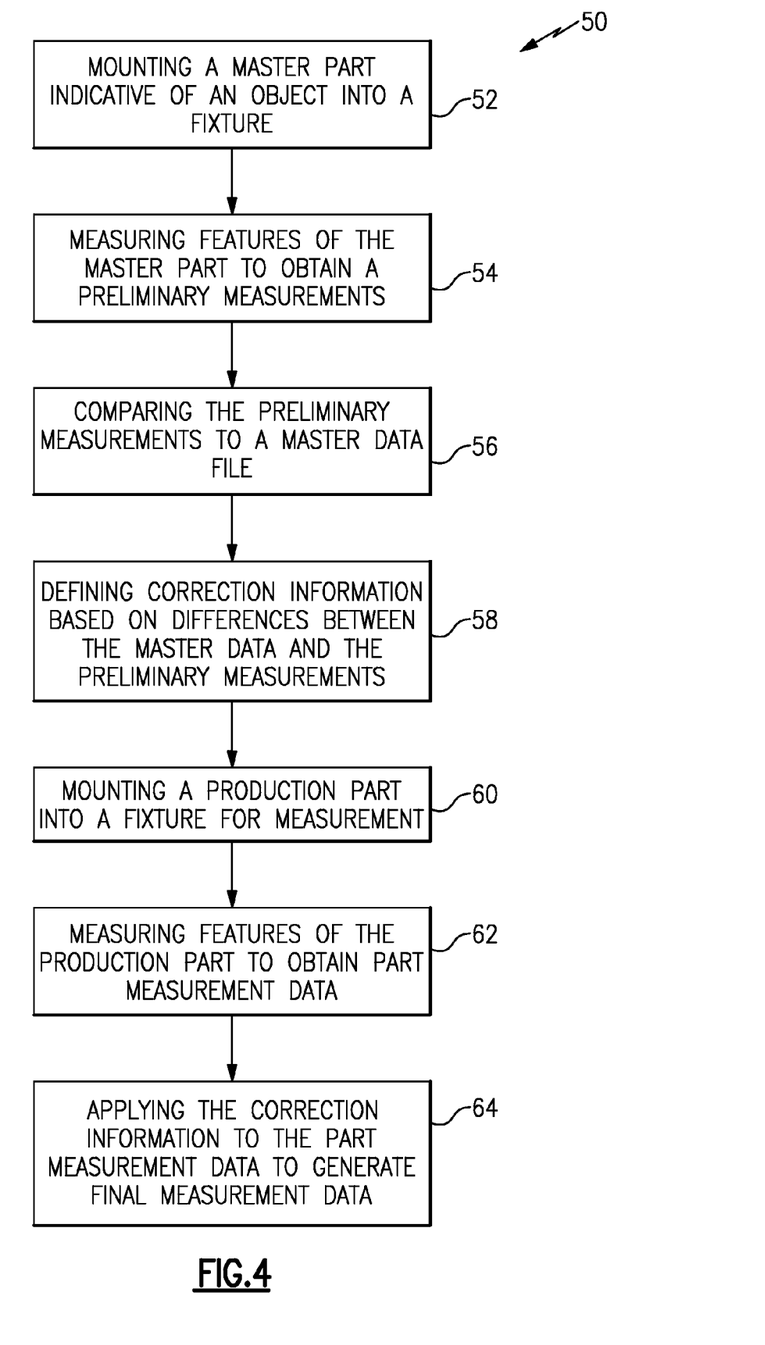
FIG. 4 is a flow diagram illustrating a process for measuring with a machine tool, in an embodiment.

Referring to FIGS. 2, 3 and 4, with continued reference to FIG. 1, an example method 50 of inspecting an object includes a first step illustrated in FIG. 2 where a master part 32 including nominal features for inspection is mounted to a fixture 20. In this example, the master part 32 represents a turbine blade and includes openings 28, surfaces 26 and air passages 30. As appreciated, components other than turbine blades are within the contemplation of this disclosure, as well as measurement of various other corresponding features.

The master part 32 is placed within a fixture 20 on a CMM 34 having a known measurement capability. The CMM 34 is then utilized to measure the master part 32 and obtain a master set of dimensional data stored as master data 36. The master data 36 is stored within a memory device such that it can be utilized and transferred to the controller 22 and used with measurement data gathered by the 5-axis machine 12.

The master data 36 includes a plurality of measurements taken of the master turbine blade 32. Multiple measurements for each feature may be utilized to create the master data 36 and provide information of a level of accuracy that is within a desired range of capability and precision.

The same master part 32 is then removed from the CMM 34 and measured on the 5-axis machine 12 having an unknown measurement capability. The measurements taken by the 5-axis machine 12 are stored in the controller 22 as preliminary measurement data 38. The preliminary measurement data 38 is compared to the master data 36 generated on the coordinate measuring machine 34 in a comparison module 40 of the controller 22. In the comparison module 40, the master data 36 and the preliminary measurement data 38 obtained from the 5-axis machine 12 are compared to generate correction information 42.

The correction information 42 includes information that quantifies differences between the master data 36 and the preliminary measurement data 38. Differences between the master data file 32 and the preliminary measurement data 38 reflect the reduced capability of the 5-axis machine 12 and are utilized to correct the preliminary measurement data 38 so that information and measurements taken on the 5-axis machine 12 can be corrected to reflect the capability of the CMM 34.

The 5-axis machine 12 may obtain multiple measurements of features of the master part 32 to generate the preliminary measurement data 38 sufficient to determine measurement consistency. Moreover, the preliminary measurement data 38 may be generated to include repeatability data and information that is indicative of the capabilities of the 5-axis machine 12. Once the repeatability of measurements taken on the 5-axis machine 12 are within desired limits; the preliminary measurement data 38 can be compared to the master data 36 in the comparison module 40 to generate the correction information 42 with a level of capability precision and accuracy desired for obtaining actual measurement data of production turbine blades.

Referring to FIG. 3, the example system 10 is then utilized to measure actual production parts 24 such as the example turbine blade. Production parts 24 will not include openings that are as precise as those found in the master part 32. The 5-axis machine 12 obtains part measurements from the production part 24 to generate a part measurement data file 44. This part measurement data file 44 is then corrected utilizing the correction information 42 obtained through use of measurements of the master part 32. The part measurement data file 44 and the correction information 42 are combined in a combination module 46 to produce complete final measurement data 48. The final measurement data 48 includes measurements from the 5-axis machine 12 that includes corrections based on the correction information 42 obtained through use and measurement of the master part 32. Accordingly, the final measurement data 48 represents measurements of the production part 24 that are substantially capable and precise to a level comparable to measurements obtained on the CMM 34.

Referring to FIG. 4, the example method 50 of inspecting an object is schematically shown and includes and begins with mounting the master part 32 indicative of features of an object into the fixture 20 of a coordinate measuring machine 34 indicated at 52.

Features of the master part 32 are measured to generate the preliminary set of dimensional data indicated at 54. The master data 36 generated by the CMM 34 is compared with preliminary measurement data 38 of the same master part 32 obtained by the 5-axis machine 12 as is indicated at 56.

The CMM 34 measures each part by first locating a desired feature or position to measure the feature and settling for a set time to allow for a very accurate measurement. The deliberate measurement progress of the CMM 34 provides for the accuracy but makes the CMM 34 ill-suited for providing measurements on production parts at production required rates.

Correction information 42 is then defined, as is indicated at 58 by comparing the preliminary measurement data 38 to the master data 36. The corrected information 42 is a result of a comparison made between master data 36 obtained on the CMM 34 for the same part that is measured on the 5-axis machine 12.

The comparison can include a statistical analysis of deviations between data sets to indicate systematic differences between measurement devices such that a repeatable and accurate correction factor can be determined and utilized. Moreover, the comparison can include any know statistical analysis technique for comparing measurement data.

Once the corrected information 42 is developed, other production parts, such as the production turbine blade indicated at 24 in FIG. 3, can be measured on the five axis machine 12. The five-axis machine 12 is much more adept and making measurements at production rates or "on-the-fly". The quicker measurement capability of the five-axis machine 12 enables measurements at speeds that correspond to production demands.

As is indicated at 60, another object, in this case the production part 24 is mounted into the fixture 20 of the five axis machine 12. The same features on the production part 24 are measured to obtain part measurement data 44 as indicated at 62. That part measurement data file 44 is then combined with the correction information 42 to obtain corrected or final measurement data 48 as indicated at 64 that can be utilized as a proper and reliable indication and verification of the location and size of the features of the production part 24.

In one example the production part 24 is a turbine blade with an airfoil including a plurality of cooling holes 28. The cooling holes 28 are measured "on-the-fly" using the 5-axis machine 12 to provide sufficiently accurate measurements of cooling hole diameter and position. The position of the cooling holes 28 is taken in view of a defined part coordinate system established by the probe 18. As appreciated other features of the production part 24 may also be measured and are within the contemplation of this disclosure.

It should be understood, that the disclosed method 50 for inspection of features of an object such as the disclosed production part 24 is performed utilizing a computing device generally noted as the controller 22 that implements various functionality required to execute the disclosed inspection, data gathering and data manipulation steps. In terms of hardware architecture, the controller 22 can include a processor, a memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the controller 22 is in operation, the processor can be configured to execute software stored within the memory, to communicate data to and from the memory, and to generally control operations of the controller 22 pursuant to the software. Software in memory, in whole or in part, is read by the processor, perhaps buffered within the processor, and then executed Accordingly, the example method and process utilizes a 5-axis machine 12 to obtain measurement data of the capability repeatability and precision desired without costly specialized measurement equipment.

Although an example embodiment has been disclosed, a worker of ordinary skill in this art would recognize that certain modifications would come within the scope of this disclosure. For that reason, the following claims should be studied to determine the scope and content of this disclosure.

What is claimed is:

1. A method of inspecting features of an object comprising:
   mounting a master part into a fixture of a first measurement machine;
   measuring the master part with the first measurement machine to obtain a master set of dimensional data for the master part, wherein the master set of dimensional data is obtained by measuring the master part on the first measurement machine with a known capability for repeating measurements within a desired range of accuracy;
   removing the master part from the first measurement machine and mounting the master part into a second measurement machine;
   measuring features of the master part to obtain a preliminary set of dimensional data with the second measurement machine, wherein the second machine facilitates movement of an inspection device along five (5) axes and the preliminary set of dimensional data is measured on the second machine along at least some of the five (5) axes;
   comparing, by a controller, the preliminary set of dimensional data from the second measuring machine with a master set of dimensional data for the master part obtained from the first measurement machine;
   generating with the controller correction information based on differences between the master set of dimensional data and the preliminary set of dimensional data and
   verifying the correction information with the controller by measuring the master part to obtain a verification set of dimensional data,
   applying the correction information to the verification set of data to generate a corrected verification data set and
   comparing the corrected verification data set to the expected data set for the master part such that the correction information is verified as meeting a desired capability responsive to a comparison between the expected data set and the corrected verification data being within a predefined range;
   measuring features of an object part that is different from the master part to obtain a first set of dimensional data; and
   applying the correction information to the first set of dimensional data to obtain a first set of corrected dimensional data for at least one feature of the object part.

2. The method as recited in claim 1, wherein measuring the features of the master part and the object part includes the step of moving a camera with a manipulator to view each feature measured.

3. The method as recited in claim 2, wherein measuring the features of the master part and the object part includes the step of moving a touch sensitive probe to each feature measured.

4. The method as recited in claim 1, wherein the preliminary set of dimensional data comprises a plurality of measurements performed on each feature of the master part.

5. The method as recited in claim 1, including obtaining data indicative of measurement repeatability of the second machine and utilizing the data indicative of measurement repeatability to define the correction information.

6. The method as recited in claim 5, wherein the correction information defines differences between measurement results obtained on the first measurement machine and measurement results obtained from the second machine.

7. The method as recited in claim 1, wherein the object part comprises an airfoil and the features comprise cooling holes and the inspection results comprise at least one of a cooling hole size and true position of the cooling holes relative to a part coordinate system.

8. An inspection system for measuring a plurality of features of a target article comprising:
   a measurement device for measuring features of an article;
   a controller for storing measurement data obtained by the measurement device, wherein the controller includes correction information and a combination module for applying the correction information to the measurement data to generate a corrected set of measurement data,
   wherein the controller further includes a comparison module for comparing a master set of measurement data obtained with a coordinate measurement machine that is different than the measurement device and a preliminary set of measurement data obtained by the measurement device generate the correction information based on results of the comparison, and
   applying the correction information to a verification set of data to generate a corrected verification data set and
   comparing the corrected verification data set to the expected data set for the master part such that the correction information is verified as meeting a desired capability responsive to a comparison between the expected data set and the corrected verification data that is within a predefined range,
   wherein the measurement device is moveable along five (5) axes and the master set of dimensional data is obtained by measuring the master part on the coordinate measurement machine with a known capability for repeating measurements within a desired range of accuracy.

9. The inspection system as recited in claim 8, wherein the measurement device is part of a machine tool different than the coordinate measurement machine and the correction information includes information indicative in a difference between measurement capabilities of the coordinate measurement machine and the machine tool.

10. The inspection system as recited in claim 9, wherein the comparison module applies a correction factor based on the correction information to measured data by the measurement device of the machine tool for generating the corrected set of measurement data within a desired range of capability.

11. The inspection system as recited in claim 9, including a master part for obtaining the master data set on the coordinate measurement machine and the preliminary data set from the machine tool.

12. The method of inspecting features of an object as recited in claim 1, wherein the master part comprises a blade for a gas turbine engine.

13. The inspection system as recited in claim 8, wherein the article comprises a blade for a gas turbine engine.

* * * * *

UNITED STATES PATENT AND TRADEMARK OFFICE
CERTIFICATE OF CORRECTION

PATENT NO. : 9,976,851 B2  
APPLICATION NO. : 13/835622  
DATED : May 22, 2018  
INVENTOR(S) : Joseph D. Drescher and Erik M. Pedersen Page 1 of 1

It is certified that error appears in the above-identified patent and that said Letters Patent is hereby corrected as shown below:

In the Claims

In Claim 1, Column 7, Line 67; replace "expected data" with --master set of dimensional data--

In Claim 1, Column 8, Line 3; replace "expected data" with --master set of dimensional data--

In Claim 7, Column 8, Line 33; replace "inspection results" with --inspected features--

In Claim 8, Column 8, Line 55-56; replace "the expected" with --an expected--

In Claim 8, Column 8, Line 56; replace "the master" with --a master--

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*